United States Patent [19]

Hetherington

[11] Patent Number: Plant 7,280

[45] Date of Patent: Jul. 24, 1990

[54] BLC. MEM. RALPH PLACENTIA C.V. TOREADOR

[75] Inventor: Ernest Hetherington, Arcadia, Calif.

[73] Assignee: Stewart Orchids, Carpinteria, Calif.

[21] Appl. No.: 276,425

[22] Filed: Nov. 25, 1988

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Howard A. Kenyon

[57] ABSTRACT

A new and distinct variety of orchid and more particularly a Brasso-laeliocattleya (Blc.) hybrid plant which is outstanding and distinct from other orchids because of its superior flowers, which combine a rare coloring, massive size, and strong carriage of flowers on a single stem. The coloring is an exceptionally warm dark rose-purple with a brilliant darker labellum shaded and veined yellow in the throat. The new variety is also distinctive from its siblings in the grex population and similar hybrids by its outstanding plant vigor. The flowers are of exceptional substance with thicker and more rigid petals than siblings of the grex. They are perfectly placed on the stem, with stem superior to its relatives in strength. The flowers have a longer bloom life and are produced more abundantly than orchids of similar breeding.

1 Drawing Sheet

DISCOVERY OF THE NEW VARIETY

The orchid of the application was discovered by the undersigned in 1978 as an outstanding member of a large sibling population of the hybrid Brassolaeliocattleya Mem. Ralph Placentia (hereinafter abbreviated Blc. Mem. Ralph Placentia). All were cultivated and bloomed at the Stewart Orchids Nursery in San Gabriel, Calif.

The crossing of Blc. Mem. Ralph Placentia from which the sibling variety 'Toreador' was selected was originally sown at the orchid nursery of Stewart Orchids at San Gabriel, Calif., June 1967. The parentage was Laeliocattleya Mem. Albert Heinecke by Brassolaeliocattleya Norman's Bay 'Lows'. Lc. Mem. Albert Heinecke was the pod parent. Blc. Norman's Bay was the pollen parent. The grex was registered by the Stewart Orchids Nursery with the Orchid Registration Committee of The Royal Horticultural Society in England in 1973 as Blc. Mem. Ralph Placentia, Stewart cross U.S. Plant Pat. No. 1,382.

The plant of this new cultivar was in time recognized as superior in its flowers to all other siblings of the population of Blc. Mem. Ralph Placentia. After the new variety had been observed, its other features of superior growth and structure were also noted. The cultivar name 'Toreador' was added to this particular plant to identify it from all other siblings of the grex.

ASEXUAL REPRODUCTION

After the 'Toreador' cultivar was discovered and named it was placed in the laboratory of Stewart Orchids for tissue propagation. During the following years, a large number of plants were asexually produced by the meristem tissue culture method. These were all asexual reproductions from the original cultivar.

All the propagations have reproduced true to the original plant in both plant and flower. A substantial cross-section have flowered. They are exactly the same as the mother clone. All plants of the new variety have continued to be readily distinguishable from both parents and from siblings of the grex Blc. Mem. Ralph Placentia.

DESCRIPTION OF THE PHOTOGRAPHS

The first photograph shows the flowers. The second photograph shows plant growth habit and number and carriage of flowers.

DESCRIPTION OF THE PLANT

The plant of the new variety is typical of a Cattleya growth habit. The leaves are strap like, unifoliate, coriacious. The leaves, at maturity, are 16 to 19 centimeters long and 6–8 centimeters wide. The plant attains a height of 35 to 45 centimeters at full maturity. The stems, flower sheaths, leaves and other parts of the plant structure are heavier and thicker in appearance than other Mem. Ralph Placentia siblings of the grex. 'Toreador' exhibits greater strength and vigor than other cultivars of the grex Mem. Ralph Placentia. The rhizome is sturdy and compact, branching off into flowering leads. The flower stem bears massive flowers with flowers separated from others without support. The flower sheath is borne in the axil of the growth with the flowers carried above the foliage.

The plants are vigorous and uniform in comparison with similar siblings or cultivars of other gregi. Blc. Mem. Ralph Placentia siblings, both in the original grex population and in the new cultivar have been virus and pathogen free during development. The cells have an even chromosome compliment, which is associated with uniform, strong, exceptional vigor. There are no characteristics of aneuploidy, or aberrant growth habit. The cultivar 'Toreador' is most likely a tetraploid with 80 chromosomes. It gives seed generously when used for hybridizing. Since its discovery, it has proven to be an outstanding parent.

DESCRIPTION OF THE FLOWERS

The outstanding and most distinguishing features of the new variety are the exceptional richness of coloring of the flowers, their fine substance, and massive size.

In the following description, the principle colors will be specified by reference to the code number of the British Horticultural Colour charts (hereinafter BHCC number), issued by the British Color Council in collaboration with The Royal Horticultural Society, dated March 1942. The sepals and petals are Tyrian Purple Sheet No. 727, Swatch 727. The lip is darker than the sepals and petals, and is most closely described as nearest to shades of dark red. The lip color varies according to light and life of the flower. The lip is veined centrally Yellow Ochre No. 07, page 7. The texture of both petals and sepals is sparkling, clear, and of radiant, intense, dark luminous coloration and of satiny texture. The intensity of color and overtones of color vary according to flower life. The flowers hold their color especially well compared with other siblings and gregi of this line of breeding. This intense, fiery ruby-like shading underlying the basic flower color is the result of crossing a dark red-purple with a bronzy-yellow Laeliocattleya. Both are tetraploids.

The flowers of the new variety Blc. Mem. Ralph Placentia 'Toreador' are larger and stronger in structure than other Mem. Ralph Placentia orchids. The flowers average 15 to 18 centimeters in width. The petals are 8–9 centimeters wide. The sepals are 3–4 centimeters wide.

The new variety generally carries two to three large flowers to the stem on a mature, well grown plant. The petals are exceptionally flat and well carried, without twisting, turning, or recurving. The sepals are in symmetrical balance with the lip and create and attractive round shape to the flower. The flowers retain their color and shape for two to three weeks, a longer time than most orchids of similar breeding. What is especially notable is the flowers intensify in color with age rather than fade or go through color changes as is often found in this line of breeding. The flowers of 'Toreador' have a strong pleasant sweet fragrance throughout their life.

The blooming season is primarily throughout summer into fall. However, the new variety will often bloom on new growths at other times of the year.

The above combination of superior characteristics of this new cultivar make it especially valuable to the commercial cut flower grower and to the connoisseur who seeks exceptional and rare beauty. It is also of special value to the orchid breeder because of its genetic make-up.

I claim:

1. A new and distinct variety of a hybrid Brassolaeliocattleya orchid, substantially as described and illustrated herein which is distinguished from siblings of this grex Blc. Mem. Ralph Placentia and other orchids by its combination of intense, dark, ruby-purple flower color, superior flower substance, size and strength in stem structure, and vigorous, reliable uniform blooming.

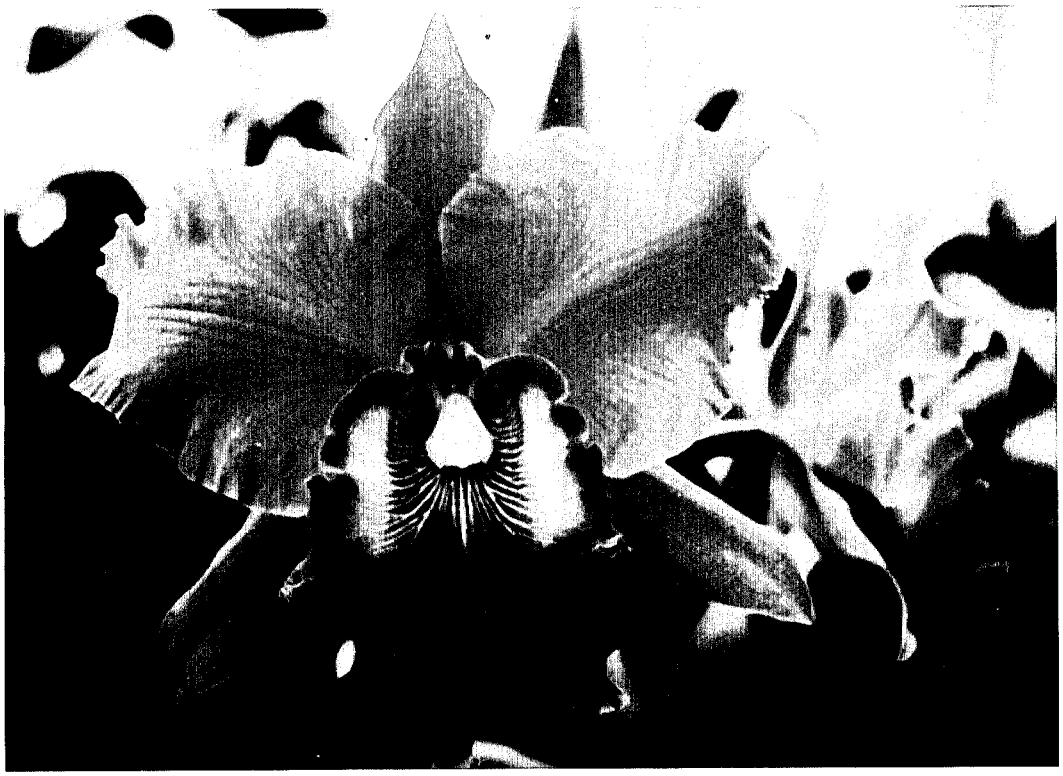
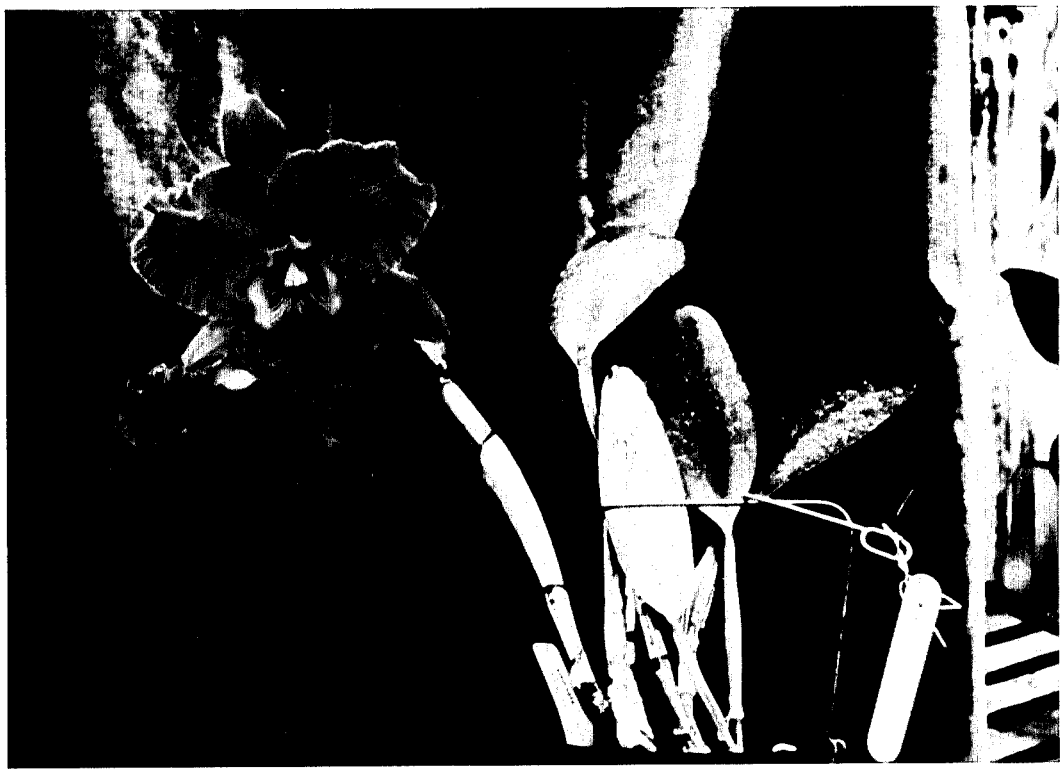

* * * * *